United States Patent [19]

Torishima et al.

[11] Patent Number: 5,326,699
[45] Date of Patent: Jul. 5, 1994

[54] SERUM-FREE MEDIUM FOR CULTURING ANIMAL CELLS

[75] Inventors: Hisashi Torishima, Osaka; Hirokuni Arakawa, Kumamoto; Ryohei Yamamoto, Takatsuki; Toyokazu Nishino, Ibaraki; Chikaaki Sakai, Neyagawa, all of Japan

[73] Assignee: Kurashiki Boseki Kabushiki Kaisha, Okayama, Japan

[21] Appl. No.: 120,235

[22] Filed: Sep. 14, 1993

Related U.S. Application Data

[63] Continuation of Ser. No. 842,980, Feb. 28, 1992, abandoned.

[30] Foreign Application Priority Data

Feb. 28, 1991 [JP] Japan ................... 3-034150

[51] Int. Cl.$^5$ ................................................ C12N 5/00
[52] U.S. Cl. .................... 435/240.2; 435/240.3; 435/240.31
[58] Field of Search ............ 435/240.2, 240.21, 240.23, 435/240.3, 240.31, 240.1

[56] References Cited

U.S. PATENT DOCUMENTS

| | | | |
|---|---|---|---|
| 4,016,036 | 4/1977 | Green et al. | 435/240.23 |
| 4,673,649 | 6/1987 | Boyce et al. | 435/240.25 |
| 4,767,704 | 8/1988 | Cleveland et al. | 435/240.3 |
| 4,940,666 | 7/1990 | Boyce et al. | 435/240.2 |

FOREIGN PATENT DOCUMENTS 0354129  2/1990  European Pat. Off. .
1283157  6/1962  France .
9007007  6/1990  World Int. Prop. O. .

OTHER PUBLICATIONS

John Paul, 6.1 Appendix 1: "Vorschriften Für Synthetische Kulturmedien," Zell–und Gewebekulturen, pp. 416–429 (1980).
Biological Abstracts, Abstract No. 41114735, Philadelphia, Pa.
Scisearch, Abstract No. EE186, Philadelphia, Pa.
ATCC Catalogue of Cell Lines and Hybudomas, 6th edition, 1988, pp. 344–355.

Primary Examiner—Douglas W. Robinson
Assistant Examiner—Susan M. Dadio
Attorney, Agent, or Firm—Wegner, Cantor, Mueller & Player

[57] ABSTRACT

The present invention provides a serum-free medium for culturing animal cells characterized in that it comprises 8.0–14.0 mg/l of methionine. Although a wide variety of animal cells can effectively be cultured by means of the serum-free medium according to the present invention, said serum-free medium produces an excellent growth effect for culturing animal epithelial cells in particular.

18 Claims, No Drawings

SERUM-FREE MEDIUM FOR CULTURING ANIMAL CELLS

This application is a continuation of U.S. application Ser. No. 07/842,980, filed Feb. 28, 1992, now abandoned.

FIELD OF THE INVENTION

The present invention relates to a serum-free medium for culturing, more particularly culturing primarily, animal cells including human cells, preferentially epithelial cells.

PRIOR ART

In many cases where animal cells are cultured in media, animal sera such as bovine serum and the like are added thereto. Therefore, extremely complex operations must be employed in order to isolate useful substances which are produced by the animal cells in extremely small quantities from the media. Even if the useful substances are isolated and purified by means of high techniques, there is a possibility that ingredients originated from the animal sera are contained in the useful substance as an impurity because the animal sera added to the media have the complicated compositions. Methods of culturing animal cells in serum-free media have been proposed as a means for solving these problems. However, the previous proposed serum-free media do not have wide applicabilities because said media are effective only for cells of specific regions of the specified animals. For example, although the complete MCDB (Molecular, Cellular and Developmental Biology) 153 medium to which prescribed amounts of epidermal growth factor and insulin are added are effective for culturing human epidermal keratinocyte (U.S. Pat. No. 4,673,649), said serum-free medium does not bring about growth effect of cells for culturing epidermal keratinocytes, various corneal epithelial cells and the like of rat and other animals.

SUMMARY OF THE INVENTION

The present invention has been carried out in order to provide a serum-free medium which brings about a superior growth effect of cells for culturing, more particularly culturing primarily, a wide variety of animal cells in comparison with the previous serum-free media for culturing animal cells.

The present invention relates to a serum-free medium for culturing animal cells characterized in that it comprises 8.0–14.0 mg/l of methionine.

DETAILED DESCRIPTION OF THE INVENTION

A characteristic feature of the present invention resides in the fact that the specified amounts, i.e. 8.0–14.0 mg/l of methionine are added to the serum-free medium. The serum-free media which comprises methionine are publicly known. However, the amounts of methionine of the previous media are less than 8.0 mg/l or more than 14.0 mg/l. For example, the amounts of methionine added to F10 medium, MCDB (Molecular, Cellular and Developmental Biology) 153 medium and DMEM (Dulbecco Minimum Essential Medium) are 4.5 mg/l, 4.476 mg/l and 30.0 mg/l respectively. Surprisingly, it has unexpectedly been found that the aforementioned problems can be solved by adding 8.0–14.0 mg/l of methionine to the serum-free medium. The expected sufficient growth effect of the cells cannot be obtained if the contents of methionine in the medium are less than 8.0 mg/l or more than 14.0 mg/l.

Other ingredients of the serum-free medium according to the present invention may suitably be selected from a wide variety of conventional ingredients used for the serum-free media for culturing animal cells by taking the kinds of animal cells to be cultured into consideration. As the ingredients which may be used in the present invention, the following amino acids, vitamins, minerals, antibiotics, growth factors and the like are exemplified. Although the contents of these ingredients are not limited, usual contents of amino acids, vitamins and minerals are 750–1500 mg/l, 50–150 mg/l and 5000–10000 mg/l respectively. Antibiotics, growth factors and other additives may suitably be added to the medium as the occasion may demand.

Amino acids: alanine, arginine.HCl, asparagine.H$_2$O, aspattic acid, cysteine HCl.H$_2$O, glutamic acid, glutamine, glycine, histidine.HCl.H$_2$O, isoleucine, leucine, lysine.HCl, methionine, phenylalanine, proline, serine, threonine, tryptophan, tyrosine, valine.

Vitamins: biotin, folic acid, lipoic acid, nicotinamide, calcium pantothenate, pyridoxine.HCl, riboflavin, thiamine, vitamin A, vitamin B$_{12}$, vitamin C, vitamin D$_3$, vitamin E, adenine, choline chloride, inositol, hypoxanthine, putrescine, thymidine, sodium pyruvate.

Minerals: Ca, K, Mg, Na, Cu, Fe, Se, Mn, Si, Mo, V, Ni, Sn, Zn.

Antibiotics: penicillin, streptomycin, kanamycin, gentamicin, amphotericin B, tylosin, aureomycin, MC-210.

Growth factors: nerve growth factor, epidermal growth factor, milk-derived growth factor, fibroblast growth factor, brain fibroblast growth factor, acidic fibroblast growth factor, platelet-derived growth factor, platelet basic protein, somatomedin, colony stimulating factor, erythropoietin, thrombopoietin, T-cell growth factor, B-cell growth factor, interleukin, cartilage-derived growth factor, bone-derived growth factor, skeletal growth factor, endothelial cell growth factor, endothelial cell-derived growth factor, eye-derived growth factor, testis-derived growth factor, Sertoli cell-derived growth factor, mammary stimulating factor, spinal cord growth factor, macrophage-derived growth factor, recycled mesodermal growth factor, transforming growth factor, tumor anglogenesis factor, osteosarcoma-derived growth factor, DNA-systhesis factor, fibroblast-derived growth factor, insulin-like growth factor, hepatocyte growth factor, 45K-growth factor, leukemia-derived growth factor, macrophage growth factor, leukemia-derived growth factor, macrophage growth factor, trophoblast-derived growth factor, hydrocortisone, insulin, transferrin, glucocorticoid, prostaglandin, cyclic adenosine monophosphate, growth hormone, adrenocorticotropic hormone, thyroid stimulating hornmone, prolactin, vasopressin, thyroxin, triiodothyronine, calcitonin, parathyroid hormone, androgen, estrogen, progesterone, glucagon, angiotensin, polyamine, lectin, cholera toxin, lesozyme chloride, colchicine, melittin, bovine pituitory extract, bovine brain extract.

The others: HEPES[N-(2-hydroxyethyl)piperazine-N'-2-ethanesulfonic acid] buffer solution, ethanolamine, phosphoethanolamine.

Among the aforementioned amino acids, particularly important amino acids are threonine, tyrosine, phenylalanine, glutamic acid, aspatic acid, lysine.HCl and serine. Ordinary contents of threonine, tyrosine, phenylalanine, glutamic acid, aspartic acid, lysine.HCl and serine are 5.0–11.5 mg/l, 7.0–11.0 mg/l, 9.0–14.5 mg/l, 400.0–500.0 mg/l, 4.0–9.5 mg/l, 19.0–28.0 mg/l, and 33.0–40.0 mg/l.

Particularly important mineral is calcium chloride and ordinary content thereof is 0.1 mM and less.

The following exemplified media I, II and III are particularly suitable for culturing animal cells, especially epithelial cells, for example, corneal epithelial cells of rabbit, epidermal keratinocytes of rat, human epidermal keratinocytes and the like.

Medium I (unit of contents of the ingredients is mg/l unless otherwise indicated)

| Ingredients | Contents | |
|---|---|---|
| Alanine | 8.91 | |
| Arginine.HCl | 210.67 | |
| Asparagine.H$_2$O | 15.01 | |
| Aspartic acid | 8.52 | |
| Cysteine.HCl.H$_2$O | 38.64 | |
| Glutamic acid | 14.70 | |
| Glutamine | 511.5 | |
| Glycine | 7.51 | |
| Histidine.HCl.H$_2$O | 44.02 | |
| Isoleucine | 51.16 | |
| Leucine | 39.35 | |
| Lysine.HCl | 23.74 | |
| Methionine | 11.19 | |
| Phenylalanine | 12.39 | |
| Proline | 23.03 | |
| Serine | 36.78 | |
| Threonine | 7.74 | |
| Tryptophan | 6.54 | |
| Tyrosine | 9.06 | |
| Valine | 19.92 | |
| Biotin | 0.020 | |
| Folic acid | 1.06 | |
| Lipoic acid | 0.21 | |
| Nicotinamide | 0.330 | |
| Calcium pantothenate | 0.620 | |
| Pyridoxine.HCl | 0.140 | |
| Riboflavin | 0.207 | |
| Thiamine.HCl | 0.675 | |
| Vitamin B$_{12}$ | 0.922 | |
| Adenine | 12.16 | |
| Choline chloride | 6.98 | |
| Glucose | 1082 | |
| Inositol | 10.81 | |
| Hypoxanthine | 2.04 | |
| Putrescine.2HCl | 0.0805 | |
| Sodium pyruvate | 55.0 | |
| Thymidine | 0.727 | |
| CaCl$_2$.2H$_2$O | 0.03 | mM |
| KCl | 201.29 | |
| MgCl$_2$.6H$_2$O | 124.0 | |
| NaCl | 7597.2 | |
| NaH$_2$PO$_4$.7H$_2$O | 294.8 | |
| KH$_2$PO$_4$ | 42.19 | |
| CuSO$_4$.5H$_2$O | 0.0025 | |
| FeSO$_4$.7H$_2$O | 1.11 | |
| Na$_2$SeO$_4$ | 0.001934 | |
| MnSO$_4$.5H$_2$O | 0.000065 | |
| Na$_2$SiO$_3$.9H$_2$O | 0.0711 | |
| (NH$_4$)$_6$Mo$_7$O$_{24}$.4H$_2$O | 0.000618 | |
| NH$_4$VO$_3$ | 0.000293 | |
| NiCl$_2$.6H$_2$O | 0.000059 | |
| SnCl$_2$.2H$_2$O | 0.000056 | |
| ZnCl$_2$.7H$_2$O | 0.2157 | |
| HEPES | 3336.2 | |
| NaHCO$_3$ | 1176 | |
| Phenol Red (Na) | 1.242 | |
| Insulin | 5 | µg/ml |
| Hydrocortisone | 0.5 | µg/ml |
| Epidermal growth factor | 10 | ng/ml |
| Bovine pituitary extract | 0.4% | (w/w) |

Medium II (unit of contents of the ingredients is mg/l unless otherwise indicated)

| Ingredients | Contents | |
|---|---|---|
| Alanine | 7.13 | |
| Arginine.HCl | 189.5 | |
| Asparagine.H$_2$O | 12.10 | |
| Aspartic acid | 7.51 | |
| Cysteine.HCl.H$_2$O | 35.13 | |
| Glutamic acid | 14.70 | |
| Glutamine | 400.0 | |
| Glycine | 6.06 | |
| Histidine.HCl.H$_2$O | 11.93 | |
| Isoleucine | 51.16 | |
| Leucine | 39.35 | |
| Lysine.HCl | 20.09 | |
| Methionine | 9.00 | |
| Phenylalanine | 9.81 | |
| Proline | 23.03 | |
| Serine | 33.00 | |
| Threonine | 5.96 | |
| Tryptophan | 6.13 | |
| Tyrosine | 7.25 | |
| Valine | 19.92 | |
| Biotin | 0.020 | |
| Folic acid | 1.06 | |
| Lipoic acid | 0.21 | |
| Nicotinamide | 0.330 | |
| Calcium pantothenate | 0.620 | |
| Pyridoxine.HCl | 0.140 | |
| Riboflavin | 0.207 | |
| Thiamine.HCl | 0.675 | |
| Vitamin B$_{12}$ | 0.922 | |
| Adenine | 12.16 | |
| Choline chloride | 6.98 | |
| Glucose | 1082 | |
| Inositol | 10.81 | |
| Hypoxanthine | 2.04 | |
| Putrescine.2HCl | 0.0805 | |
| Sodium pyruvate | 55.0 | |
| Thymidine | 0.727 | |
| CaCl$_2$.2H$_2$O | 0.03 | mM |
| KCl | 201.29 | |
| MgCl$_2$.6H$_2$O | 124.0 | |
| NaCl | 7597.2 | |
| NaH$_2$PO$_4$.7H$_2$O | 294.8 | |
| KH$_2$PO$_4$ | 42.19 | |
| CuSO$_4$.5H$_2$O | 0.0025 | |
| FeSO$_4$.7H$_2$O | 1.11 | |
| Na$_2$SeO$_4$ | 0.001934 | |
| MnSO$_4$.5H$_2$O | 0.000065 | |
| Na$_2$SiO$_3$.9H$_2$O | 0.0711 | |
| (NH$_4$)$_6$Mo$_7$O$_{24}$.4H$_2$O | 0.000618 | |
| NH$_4$VO$_3$ | 0.000293 | |
| NiCl$_2$.6H$_2$O | 0.000059 | |
| SnCl$_2$.2H$_2$O | 0.000056 | |
| ZnCl$_2$.7H$_2$O | 0.2157 | |
| HEPES | 3336.2 | |
| NaHCO$_3$ | 176 | |
| Phenol Red (Na) | 1.242 | |
| Insulin | 5 | µg/ml |
| Hydrocortisone | 0.5 | µg/ml |
| Epidermal growth factor | 10 | ng/ml |
| Bovine pituitary extract | 0.4% | (w/w) |

Medium III (Unit of contents of the ingredients is mg/l unless otherwise indicated)

| Ingredients | Contents |
|---|---|
| Alanine | 4.46 |
| Arginine.HCl | 168.54 |
| Aparagine.H$_2$O | 7.51 |
| Apartic acid | 8.52 |
| Cysteine.HCl.H$_2$O | 36.88 |
| Glutamic acid | 14.70 |
| Glutamine | 550.0 |
| Glycine | 3.75 |
| Histidine.HCl.H$_2$O | 54.50 |
| Isoleucine | 77.40 |

-continued

| Ingredients | Contents | |
|---|---|---|
| Leucine | 59.03 | |
| Lysine.HCl | 23.74 | |
| Methionine | 13.00 | |
| Phenylalanine | 14.00 | |
| Proline | 17.27 | |
| Serine | 31.53 | |
| Threonine | 10.00 | |
| Tryptophan | 11.23 | |
| Tyrosine | 11.00 | |
| Valine | 41.00 | |
| Biotin | 0.0075 | |
| Folic acid | 0.88 | |
| Lipoic acid | 0.10 | |
| Nicotinamide | 0.513 | |
| Calcium pantothenate | 0.762 | |
| Pyridoxine.HCl | 0.514 | |
| Riboflavin | 0.075 | |
| Thiamine.HCl | 0.675 | |
| Vitamin $B_{12}$ | 0.205 | |
| Adenine | 12.16 | |
| Choline chloride | 6.98 | |
| Glucose | 1045 | |
| Inositol | 21.62 | |
| Putrescine.2HCl | 0.08 | |
| Thymidine | 0.36 | |
| $CaCl_2.2H_2O$ | 0.03 | mM |
| KCl | 260.9 | |
| $MgCl_2.6H_2O$ | 61.0 | |
| NaCl | 7597.2 | |
| $NaH_2PO_4.7H_2O$ | 141.96 | |
| $CuSO_4.5H_2O$ | 0.0025 | |
| $FeSO_4.7H_2O$ | 1.70 | |
| $Na_2SeO_4$ | 0.001934 | |
| $MnSO_4.5H_2O$ | 0.000121 | |
| $Na_2SiO_3.9H_2O$ | 0.0711 | |
| $(NH_4)_6Mo_7O_{24}.4H_2O$ | 0.000618 | |
| $NH_4VO_3$ | 0.000293 | |
| $NiCl_2.6H_2O$ | 0.000059 | |
| $SnCl_2.2H_2O$ | 0.000056 | |
| $ZnCl_2.7H_2O$ | 0.072 | |
| HEPES | 3336.2 | |
| $NaHCO_3$ | 1176 | |
| Phenol Red (Na) | 1.13 | |
| Insulin | 5 | μg/ml |
| Hydrocortisone | 0.5 | μg/ml |
| Epidermal growth factor | 10 | ng/ml |
| Bovine pituitory extract | 0.4% | (w/w) |

The aforementioned serum-free media are extremely effective not only for a culture, more particularly primary culture, of animal epithelial cells, but also a subculture and freezing preservation of epidermal keratinocytes and corneal epithelial cells of rat and other animals, the subculture of these animal cells in the prior serum-containing media such as DMEM, MEM and the like to which sera are added being difficult.

Although the serum-free medium according to the present invention is particularly useful for culturing animal epithelial cells, it is effective for culturing other cell lines such as endothelial cells, fibroid cells, neurocytes, immunocytes, endocrinal cells and the like.

EXAMPLES

The present invention will be illustrated by the following examples.

EXAMPLE 1

Corneal epithelial cells separated from bulbus oculi of a rabbit were cultured in the aforesaid medium I at 37° C. for 5 days and then inoculated to a culture plate having 24 wells (5000 cells/well). The inoculated cells were cultured in the medium I at 37° C. for 5 days. Remarkable growth effect of the cells was obtained (35,000 cells/well).

COMPARATIVE EXAMPLES 1-3

Cultures of the corneal epithelial cells were carried out according to the same manner as that described in Example 1 except that the following media MCDB 153, DMEM and F-10 were employed instead of the medium I. Growth effects of the cells were scarcely obtained (6000-7000 cells/well).

MCDB153 Medium (Unit of contents of the ingredients is mg/l unless otherwise indicated)

| Ingredients | Contents | |
|---|---|---|
| Alanine | 8.91 | |
| Arginine.HCl | 210.7 | |
| Asparagine.$H_2O$ | 15.01 | |
| Aspartic acid | 3.99 | |
| Cysteine.HCl.$H_2O$ | 42.04 | |
| Glutamic acid | 14.71 | |
| Glutamine | 877.2 | |
| Glycine | 7.51 | |
| Histidine.HCl.$H_2O$ | 16.77 | |
| Isoleucine | 1.968 | |
| Leucine | 65.6 | |
| Lysine.HCl | 18.27 | |
| Methionine | 4.476 | |
| Phenylalanine | 4.956 | |
| Proline | 34.54 | |
| Serine | 63.05 | |
| Threonine | 11.9 | |
| Tryptophan | 3.06 | |
| Tyrosine | 2.718 | |
| Valine | 35.13 | |
| Biotin | 0.015 | |
| Folic acid | 0.79 | |
| Lipoic acid | 0.206 | |
| Nicotinamide | 0.037 | |
| Calcium pantothenate | 0.476 | |
| Pyridoxine.HCl | 0.062 | |
| Riboflavin | 0.038 | |
| Thiamine.HCl | 0.337 | |
| Vitamin $B_{12}$ | 0.41 | |
| Adenine | 24.32 | |
| Choline chloride | 13.96 | |
| Glucose | 1081 | |
| Inositol | 18.02 | |
| Putrescine.2HCl | 0.161 | |
| Sodium pyruvate | 55.0 | |
| Thymidine | 0.727 | |
| $CaCl_2.2H_2O$ | 0.03 | mM |
| KCl | 111.83 | |
| $MgCl_2.6H_2O$ | 122.0 | |
| NaCl | 7597.2 | |
| $NaH_2PO_4.7H_2O$ | 536.2 | |
| $CuSO_4.5H_2O$ | 0.00275 | |
| $FeSO_4.7H_2O$ | 1.39 | |
| $H_2SeO_3$ | 0.003867 | |
| $MnSO_4.5H_2O$ | 0.000241 | |
| $Na_2SiO_3.9H_2O$ | 0.1421 | |
| $(NH_4)_6Mo_7O_{24}.4H_2O$ | 0.001236 | |
| $NH_4VO_3$ | 0.000585 | |
| $NiCl_2.6H_2O$ | 0.000119 | |
| $SnCl_2.2H_2O$ | 0.000113 | |
| $ZnCl_2.7H_2O$ | 0.1438 | |
| HEPES | 6672.4 | |
| $NaHCO_3$ | 1176 | |
| Phenol Red (Na) | 1.242 | |
| $CH_3COONa.3H_2O$ | 500 | |

DMEM (Unit of contents of the ingredients is mg/l unless otherwise indicated)

| Ingredients | Contents |
|---|---|
| Arginine.HCl | 84.0 |
| Cysteine.2Na | 56.8 |
| Glutamine | 584.0 |
| Glycine | 30.0 |
| Histidine.HCl.$H_2O$ | 42.0 |

-continued

| Ingredients | Contents |
| --- | --- |
| Isoleucine | 104.8 |
| Leucine | 104.8 |
| Lysine.HCl | 146.2 |
| Methionine | 30.0 |
| Phenylalanine | 66.0 |
| Serine | 42.0 |
| Threonine | 95.2 |
| Tryptophan | 16.0 |
| Tyrosine | 72.0 |
| Valine | 93.6 |
| Lipoic acid | 4.0 |
| Nicotinamide | 4.0 |
| Calcium pantothenate | 4.0 |
| Pyridoxine.HCl | 4.0 |
| Riboflavin | 0.4 |
| Thiamine.HCl | 4.0 |
| Choline chloride | 4.0 |
| Glucose | 4500.0 |
| Inositol | 7.0 |
| Sodium pyruvate | 110.0 |
| $CaCl_2$ | 1.8 mM |
| KCl | 400.0 |
| $MgCl_2$ | 97.7 |
| NaCl | 6800.0 |
| $NaH_2PO_4.H_2O$ | 140.0 |
| $NaHCO_3$ | 2000.0 |
| Phenol Red (Na) | 10.0 |

F10 Medium (Unit of contents of the ingredients is mg/l unless otherwise indicated)

| Ingredients | Contents |
| --- | --- |
| Alanine | 8.9 |
| Arginine.HCl | 210.7 |
| Asparagine.$H_2O$ | 15.0 |
| Aspartic acid | 13.3 |
| Cysteine.HCl.$H_2O$ | 35.1 |
| Glutamic acid | 14.7 |
| Glutamine | 146.2 |
| Glycine | 7.5 |
| Histidine.HCl.$H_2O$ | 21.0 |
| Isoleucine | 2.6 |
| Leucine | 13.1 |
| Lysine.HCl | 29.3 |
| Methionine | 4.5 |
| Phenylalanine | 5.0 |
| Proline | 11.5 |
| Serine | 10.5 |
| Threonine | 3.6 |
| Tryptophan | 0.6 |
| Tyrosine | 1.8 |
| Valine | 3.5 |
| Biotin | 0.02 |
| Folic acid | 1.32 |
| Lipoic acid | 0.21 |
| Nicotinamide | 0.61 |
| Calcium pantothenate | 0.72 |
| Pyridoxine.HCl | 0.21 |
| Riboflavin | 0.38 |
| Thiamine.HCl | 1.01 |
| Vitamin $B_{12}$ | 1.36 |
| Choline chloride | 0.7 |
| Glucose | 1100.0 |
| Inositol | 0.54 |
| Hypoxanthine | 4.08 |
| Sodium pyruvate | 110.0 |
| Thymidine | 0.73 |
| $CaCl_2.2H_2O$ | 0.3 mM |
| KCl | 285.0 |
| $MgCl_2$ | 74.6 |
| NaCl | 7400.0 |
| $KH_2PO_4$ | 83.0 |
| $CuSO_4$ | 0.002 |
| $FeSO_4$ | 0.46 |
| $NaHCO_3$ | 1200.0 |
| Phenol Red (Na) | 1.24 |
| $Na_2HPO_4$ | 156.2 |

-continued

| Ingredients | Contents |
| --- | --- |
| $ZnSO_4.7H_2O$ | 0.03 |

EXAMPLE 2

Corneal epithelial cells separated from bulbus oculi of a rabbit were inoculated to a culture plate having 24 wells (5000 cells/well) and then the inoculated cells were cultured in the aforementioned medium II at 37° C. for 5 days. Remarkable growth effect of the cells was obtained (31,000 cells/well).

EXAMPLE 3

Culture of the corneal epithelial cells of the rabbit was carried out according to the same manner as that described in Example 2 except that the aforesaid mediun III was employed instead of the medium II. Remarkable growth effect of the cells was obtained (32,000 cells/well).

EXAMPLE 4

Epidermal cells separated from epidermis of a newly born rat were cultured in a medium I' which has the same composition as that of the medium I except that it comprises 20 ng/ml of cholera toxin and 0.075 mM of calcium chloride at 37° C. for 5 days and inoculated into T-25 flask (125,000 cells/flask). The inoculated cells were cultured in the medium I' at 37° C. for 7 days and 1,400,000 cells were obtained.

COMPARATIVE EXAMPLES 4-6

Cultures of the corneal epithelial cells were carried out according to the same manner as that of Example 3 except that the inoculated cells were cultured in the medium MCDB 153, DMEM or F-10. In the case where MCDB153 was used, 750,000 cells were obtained. In the case where DMEM or F-10 was employed, the cells were exfoliated from the adhered surface of the culture vessel and were not grown.

EXAMPLE 5

Epidermal keratinocytes separated from epidermis of a newly born rat were inoculated into T-25 flask (125,000 cells/flask). The inoculated cells were cultured at 37° C. for 9 days in the medium I" which has the same composition as that of the medium I' with the exception that it does not comprise bovine pituitary extract. Growth effect of the cells was observed (1,500,000 cells/flask).

COMPARATIVE EXAMPLE 7

Culture of the epidermal keratinocytes of rat was carried out according to the same manner as that of Example 5 except that MCDB 153 was employed instead of the medium I". On the course of the culture, growth of the cells was stopped.

EXAMPLE 6

Human epidermal keratinocytes were cultured in accordance with the procedure of Example 5. The substantially same growth effect of the cells as that of Example 5 was obtained.

Although a wide variety of animal cells can effectively be cultured, more particularly cultured primarily, by means of the serum-free medium according to the present invention, said serum-free medium produces an excellent growth effect for culturing animal epithelial cells in particular.

We claim:

1. A serum-free medium for culturing animal epithelial cells comprising 9.0–14.0 mg/l of methionine, 5.0–11.5 mg/l of threonine, 7.0–11.0 mg/l of tyrosine, 9.0–14.5 mg/l of phenylalanine, 400.0–550.0 mg/l of glutamine, 7.0–9.5 mg/l of aspartic acid, 19.0–28.0 mg/l of lysine HCl, 33.0–40.0 mg/l of serine, and up to 0.1 mM of Ca in the form of calcium chloride; and one or more conventional ingredients selected from the group consisting of glucose, vitamins, minerals, growth factors, HEPES, and amino acids other than the foregoing listed amino acids.

2. The serum-free medium of claim 1, wherein the other amino acids are selected from the group consisting of alanine, arginine, asparagine, cysteine, glutamic acid, glycine, histidine, isoleucine, leucine, proline, tryptophan, valine, and alkaline salts or acid salts thereof.

3. The serum-free medium of claim 1, wherein the vitamins are selected from the group consisting of biotin, folic acid, lipoic acid, nicotinamide, pantothenic acid, pyridoxine, riboflavin, thiamine, vitamin $B_{12}$, adenine, choline chloride, inositol, hypoxanthine, putrescine, pyruvic acid, thymidine, and alkaline salts or acid salts thereof.

4. The serum-free medium of claim 1, wherein the minerals are selected from the group consisting of Ca, K, Mg, Na, Cu, Fe, Se, Mn, Si, Mo, V, Ni, Sn, and Zn.

5. The serum-free medium of claim 1, wherein the growth factors are selected from the group consisting of insulin, hydrocortisone, epidermal growth factor, and bovine pituitary extract.

6. The serum-free medium of claim 1, wherein the medium additionally contains phenol red (Na).

7. A serum free medium for culturing animal epithelial cells which comprises 9.0–14.0 mg/l of methionine, 5.0–11.5 mg/l of threonine, 7.0–11.0 mg/l of tyrosine, 9.0–14.5 mg/l of phenylalanine, 400.0–550.0 mg/l of glutamine, 7.0–9.5 mg/l of aspartic acid, 19.0–28.0 mg/l of lysine HCl, 33.0–40.0 mg/l of serine, 0.1 mM or less of calcium chloride; alanine, arginine HCl, asparagine $H_2O$, cysteine HCl $H_2O$, glutamic acid, glycine, histidine HCl $H_2O$, isoleucine, leucine, proline, tryptophan, valine, biotin, folic acid, lipoic acid, nicotinamide, calcium pantothenate, pyridoxine HCl, riboflavin, thiamine HCl, vitamin $B_{12}$, adenine, choline chloride, inositol, hypoxanthine, putrescine HCl, sodium pyruvate, thymidine, KCl, $MgCl_2 6H_2O$, NaCl, $NaH_2PO_4 7H_2O$, $KH_2PO_4$, $CuSO_4 5H_2O$, $FeSO_4 7H_2O$, $Na_2SeO_4$, $MnSO_4 5H_2O$, $Na_2SiO_3 9H_2O$, $(NH_4)_6Mo_7O_{24} 4H_2O$, $NH_4VO_3$, $NiCl_2 6H_2O$, $SnCl_2 2H_2O$, $ZnSO_4 7H_2O$, $NaHCO_3$ glucose, HEPES, phenol red (Na), insulin, hydrocortisone, epidermal growth factor, and bovine pituitary extract.

8. The serum-free medium of claim 1, wherein the epithelial cells are epidermal keratinocytes or corneal epithelial cells.

9. The serum-free medium of claim 1, in which the culture is primary culture.

10. The serum-free medium of claim 1, wherein the epithelial cells are corneal epithelial cells.

11. A method of culturing animal corneal epithelial cells comprising culturing said cells in a serum-free medium comprising 9.0–14.0 mg/l of methionine, 5.0–11.5 mg/l of threonine, 7.0–11.0 mg/l of tyrosine, 9.0–14.5 mg/l of phenylalanine, 400.0–550.0 mg/l of glutamine, 7.0–9.5 mg/l of aspartic acid, 19.0–28.0 mg/l of lysine HCl, 33.0–40.0 mg/l of serine, and up to 0.1 mM of Ca in the form of calcium chloride; and one or more conventional ingredients selected from the group consisting of glucose, vitamins, minerals, growth factors, HEPES, and amino acids other than the foregoing listed amino acids.

12. The method of claim 11, wherein the other amino acids are selected from the group consisting of alanine, arginine, asparagine, cysteine, glutamic acid, glycine, histidine, isoleucine, leucine, proline, tryptophan, valine, and alkaline salts or acid salts thereof.

13. The method of claim 11, wherein the vitamins are selected from the group consisting of biotin, folic acid, lipoic acid, nicotinamide, pantothenic acid, pyridoxine, riboflavin, thiamine, vitamin $B_{12}$, adenine, choline chloride, inositol, hypoxanthine, putrescine, pyruvic acid, thymidine, and alkaline salts or acid salts thereof.

14. The method of claim 11, wherein the minerals are selected from the group consisting of Ca, K, Mg, Na, Cu, Fe, Se, Mn, Si, Mo, V, Ni, Sn, and Zn.

15. The method of claim 11, wherein the growth factors are selected from the group consisting of insulin, hydrocortisone, epidermal growth factor, and bovine pituitary extract.

16. The method of claim 11, wherein the medium additionally contains phenol red (Na).

17. A method of culturing animal corneal epithelial cells which comprises culturing said cells in a serium-free medium comprising 9.0–14.0 mg/l of methionine, 5.0–11.5 mg/l of threonine, 7.0–11.0 mg/l of tyrosine, 9.0–14.5 mg/l of phenylalanine, 400.0–550.0 mg/l of glutamine, 7.0–9.5 mg/l of aspartic acid, 19.0–28.0 mg/l of lysine HCl, 33.0–40.0 mg/l of serine, 0.1 mM or less of calcium chloride; alanine, arginine HCl asparagine $H_2O$, cysteine HCl $H_2O$, glutamic acid, glycine, histidine HCl $H_2O$, isoleucine, leucine, proline, tryptophan, valine, biotin, folic acid, lipoic acid, nicotinamide, calcium pantothenate, pyridoxine HCl, riboflavin, thiamine HCl, vitamin $B_{12}$, adenine, choline chloride, inositol, hypoxanthine, putrescine HCl, sodium pyruvate, thymidine, KCl, $MgCl_2 6H_2O$, NaCl, $NaH_2PO_4 7H_2O$, $KH_2PO_4$, $CuSO_4 5H_2O$, $FeSO_4 7H_2O$, $Na_2SeO_4$, $MnSO_4 5H_2O$, $Na_2SiO_3 9H_2O$, $(NH_4)_6Mo_7O_{24} 4H_2O$, $NH_4VO_3$, $NiCl_2 6H_2O$, $SnCl_2 2H_2O$, $ZnSO_4 7H_2O$, $NaHCO_3$, glucose, HEPES, phenol red (Na), insulin, hydrocortisone, epidermal growth factor, and bovine pituitary extract.

18. The method of claim 17 further comprising the steps of subculturing the cells in the serum-free medium.

* * * * *